Dec. 27, 1966 A. P. HOWARD Plant Pat. 2,696
ROSE PLANT
Filed Sept. 27, 1965
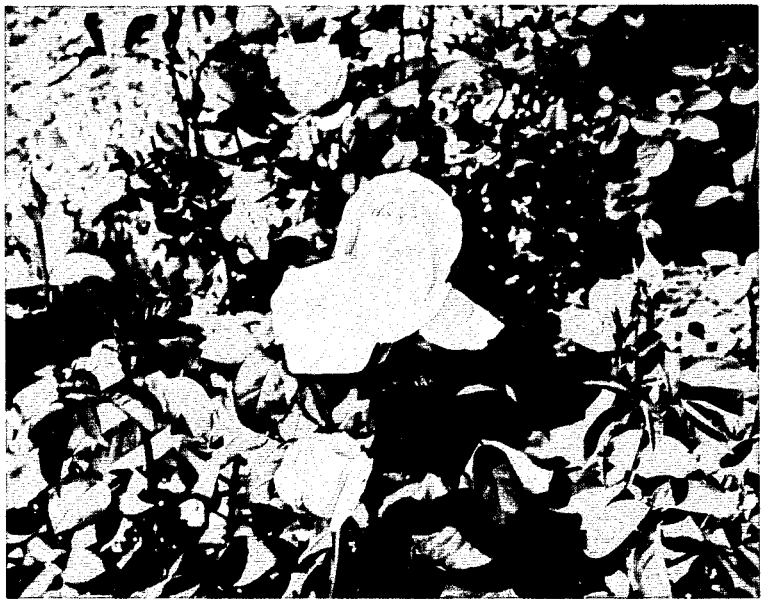
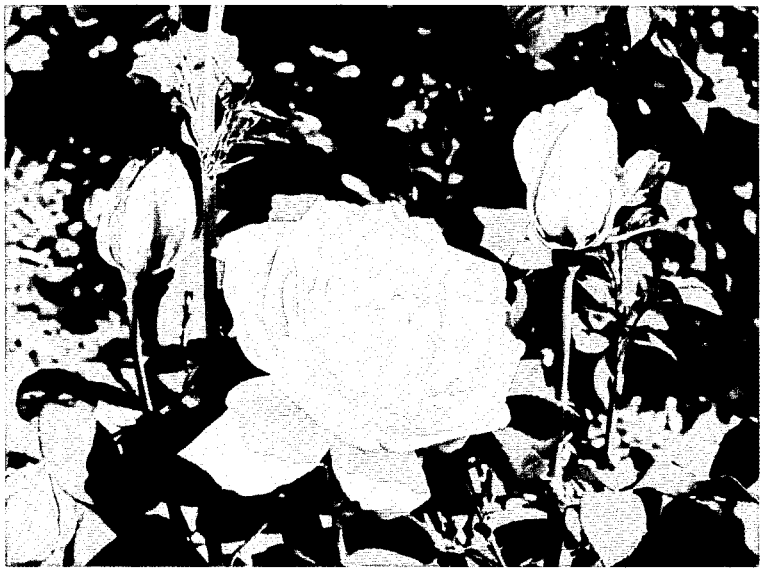
INVENTOR
ARTHUR P. HOWARD
BY J. F. Cuneo
ATTORNEY United States Patent Office Plant Pat. 2,696
Patented Dec. 27, 1966

2,696
ROSE PLANT

Arthur P. Howard, Sierra Madre, Calif., assignor to Paul J. Howard Co., Inc., Los Angeles, Calif., a corporation of California Filed Sept. 27, 1965, Ser. No. 490,755
1 Claim. (Cl. Plt.—19)

This invention relates to a new and distinct variety of rose plant that is ordinarily classified as a hybrid tea rose.

The plant resulted from cross-breeding of Charlotte Armstrong, a patented rose bearing United States Patent No. 455, with Heart's Desire, a patented variety of rose, United States Plant Patent No. 501, after numerous experiments conducted by me in Montebello, California. The original plant was produced by me in 1955, using Charlotte Armstrong as the seed parent, and Heart's Desire as the pollen parent.

The flowers produced by the new variety of rose plant are pink, from compact buds that open to form very large blooms that are at the end of very long stems. The flowers are produced in abundance during the growing season that extends from March to November in the coastal region of southern California. The plant forms a large, well branched bush.

In comparing the blooms of my new variety with those of its seed parent, Charlotte Armstrong, the flowers are a Phlox Pink, whereas those of the seed parent are a light red. Compared to its pollen parent Heart's Desire, the showy Phlox Pink flowers differ considerably from the flowers of the pollen parent that are best described as a dark red. The plant is very hardy, exhibiting a vigorous upright growth habit; some of the plants have been observed to reach a height of six or more feet.

The new rose belongs to the outdoor bush type and is used primarily for cut flowers and for garden ornamentation. The plant has been reproduced asexually by budding performed in Montebello, California. The plant and flowers resulting, are reproduced true, with all of the distinguishing characteristics being transmitted through the succeeding propagations of the variety; the plant cannot be reproduced true from seed.

The accompanying illustrations in full color show a typical specimen of buds and a partially opened flower in the upper view, with foliage, and the lower view shows the foliage with a fully opened bloom as well as buds in various stages of development. The colors are as true as it is possible to reproduce them by this type of color representation.

A detailed description of the new variety of rose follows, and to facilitate identification of the important colors described in this specification, the designations adopted by the British Horticultural Colour Charts have been followed.

The new rose belongs to the outdoor bush type and is of the so-called hybrid tea class. It's beautiful, large, rich pink flowers borne singly on very long stems make it particularly desirable for cut flowers and the large tall bush makes the plant a great asset to any garden.

*The flower*

Locality where grown and observed: Montebello, California, Los Angeles, California, and West Los Angeles, California.

Flowers borne: Flowers are borne mainly as single flowers on long stems that vary from eighteen to twenty-four inches in length.

Number of blooms: When grown outdoor the plant produces an abundance of flowers, there being as many as fifty blooms on the plant at one time.

Continuity: The plant blooms continually from March to November in the coastal region of southern California. The maximum flowering occurs in April, May and June and again in September, October and November.

Fragrance: This variety of rose has a moderate, delicate fragrance which is more noticeable when the humidity is high.

Bud:

*Peduncle.*—Length: Varies from three and one-half to five inches. Color: Reddish-brown.

*Before calyx breaks.*—Size: About three-quarters of an inch in diameter. Form: Pointed and could probably be described as conical.

*As calyx breaks.*—Color: Ruby Red 827. Sepals: Shape—almond shaped with a pointed apex; size—about one and three-quarters inches in length with the largest width of the sepal being about one inch.

*As first petal opens.*—Size: Two and one-half inches in length with a width that varies from two and one-quarter to two and one-half inches. The petals are slightly reflex. Color: Inside and outside—the color is between Fuchsine Pink 627 and Fuchsine Ping 627/1. At the base of each petal there is a small area that Uranium Green 63. Form: Round with a slight tip at the apex. The margin is substantially entire. Opening: Opening is slow but the flower opens well and this is not affected very much by the weather.

Bloom:

*Size.*—Flowers are from five and one-half to six inches in diameter.

*Petalage.*—Number of petals varies from 30 to 35.

*Form.*—High centered, robust, becoming globular with the inner petals somewhat smaller than the outer petals.

*Petals.*—Texture: Waxy and quite thick.

*Shape.*—The outer petals are substantially round. The petals become more oval as they progress inwardly.

*Color.*—Tip: Inside—Phlox Pink 625; outside—Phlox Pink 625/1. Center and base: Inside—Phlox Pink 625 merging into Uranium Green 63 at base; outside—Phlox Pink 625/1 merging into Uranium Green 63 at base.

*General color effect.*—The general overall color effect is between Phlox Pink 625 and Phlox Pink 625/1.

*Behaviour.*—Petals drop off clean. The flower is not appreciably affected by hot weather.

Flower longevity: The flowers last from seven to ten days on the plant. Cut flowers also appear to last from seven to ten days.

*Reproductive organs*

Stamens: Average number varies from thirty to fifty.

Filaments: Filaments are from one-half to five-eighths of an inch in length. Color—reddish-gold.

Anthers: Anthers are prominent. Color—golden yellow.

Pollen:

*Quantity.*—Moderate.

*Color.*—Golden yellow.

Pistils: Very numerous.

Styles: Not too prominent. Size and arrangement—the styles are moderately even and have a length between short and medium; the styles are bunched.

Stigma: Color—white.

Ovaries: Ovaries are enclosed in the calyx.

Hips:

*Length.*—About three-quarters of an inch.

*Form.*—Somewhat pear shaped; could be described as pyriform.

*Color.*—Light green.

Seeds: No seeds have been observed.

*The plant*

Foliage:

*Leaves.*—Compound, odd-pinnate leaves having an average of five leaflets with occasionally a compound leaf having seven leaflets. Quantity: Heavy. Leaflets: Shape—ovate with tip mucronate having an obtuse base; the margins are serrate; size—the leaflets are two and one-half inches long and approximately two inches wide; color—top, Parsley Green oo962; underside, Spinach Green o960/3. Young leaflets: Color—approximately the same color as mature leaflets except that these have a pronounced reddish cast. Type: Imparipinnate.

Stipules: Prominent, being from one-half to five-eighths inches.

Growth: Habit and height—upright and well branched. Plant grows from five to seven feet in height. The plant has a good productivity and is a vigorous grower.

Canes: The diameter of the canes varies from three-quarters to one inch when the plant is fully established.

Main stems:

*Length.*—Some main stems reach from two to three feet in length and occasionally one will reach four feet.

*Color.*—Brownish-green.

*Prickles (large).*—Size and number: Prickles are substantially straight and husky. They are not too numerous and are about one-quarter of an inch in length.

*Prickles (small).*—The plant has so few that usually these could be classed as none.

Branches:

*Color.*—Reddish-green.

*Shape.*—Predominantly vertical.

*Hair.*—None.

*Thorns.*—Number and size: Thorns are few and are about one-quarter inch in length. These are well spaced.

*Small prickles.*—None

New shoots:

*Color.*—Bronzy red.

*Large and small prickles.*—None.

Having described my invention, I claim:

The new and distinct variety of rose plant of the class designated as hybrid tea roses, substantially as herein shown and described, characterized particularly as to novelty by its Phlox Pink blooms that are very large and borne at the end of very long stems, the small number of prickles and thorns, the longevity of the flowers after they have been cut, the tall, vigorous, upright, well branched growth of the plant, and its large, attractive foliage.

No references cited.

ABRAHAM G. STONE, *Primary Examiner.*

R. E. BAGWILL, *Assistant Examiner.*